United States Patent [19]

Rigbi et al.

[11] 4,118,575

[45] Oct. 3, 1978

[54] DERIVATIVES OF PARA-GUANIDINO-L-PHENYLALANINE AND METHODS OF PREPARING THEM

[75] Inventors: Meir Rigbi; Yakir Klausner, both of Jerusalem, Israel; Pierre Lefrancier; Edgar Sache, both of Bures s, Yvette, France

[73] Assignee: Choay S.A., Paris, France

[21] Appl. No.: 610,671

[22] Filed: Sep. 5, 1975

[30] Foreign Application Priority Data

Sep. 9, 1974 [FR] France ............................. 74 30509

[51] Int. Cl.$^2$ ...................... C07C 149/40; C12K 1/04
[52] U.S. Cl. ........................................ 560/13; 424/94; 195/103.5 R; 562/430; 562/439
[58] Field of Search ........................ 260/470; 560/13

[56] References Cited

U.S. PATENT DOCUMENTS

| 3,622,615 | 11/1971 | Nicolaides et al. ................ 260/470 |
| 3,852,338 | 10/1971 | Kaiser et al. ...................... 260/470 |

FOREIGN PATENT DOCUMENTS

1,268,867  3/1972  United Kingdom ................... 260/470

OTHER PUBLICATIONS

Fieser, Experiments in Org. Chemistry, D.C. Heath and Co., Boston, 3rd Ed. Rev. (1955), pp. 90-91.
Jameson et al., Biochem. J. (1973), 131, 107-117.
Hickinbottom, Reactions of Organic Compounds, Longmans, Green & Co., New York (1950), 100.
Weygand, Organic Preparations, Interscience Publishers Inc., New York (1945), 174.

*Primary Examiner*—Howard T. Mars
*Attorney, Agent, or Firm*—Weiser, Stapler & Spivak

[57] ABSTRACT

The invention relates to novel derivatives of L-phenylalanine and particularly to tosyl-paraguanidino-L-phenylalanine methyl ester, to ter-butyloxycarbonyl derivative of para-guanidino-L-phenylalanine and to para-guanidino-L-phenylalanine.

The tosyl-paraguanidino-L-phenylalanine methyl ester is an efficient trypsine substrate.

3 Claims, No Drawings

DERIVATIVES OF PARA-GUANIDINO-L-PHENYLALANINE AND METHODS OF PREPARING THEM

The invention relates to novel derivatives of L-phenylalanine.

A prefered derivative of L-phenylalanine consists of the tosyl-paraguanidino-L-phenylalanine methyl ester, having the formula:

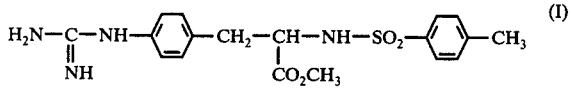

The invention also relates to the salts, such as the hydrochloride, of the novel compound according to the invention.

This novel compound according to the invention is a particularly efficient trypsin substrate and is therefore a very valuable laboratory reagent for assaying trypsin.

The invention also relates to a method of preparing this compound, which process comprises esterifying tosyl-paraguanidino-L-phenylalanine, having the formula:

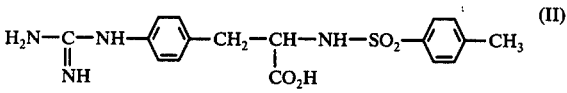

with methanol.

The invention also relates to novel derivatives of L-phenylalanine, which form valuable intermediates for the preparation of the compound of formula II.

The new derivatives according to the invention are characterised by the formula

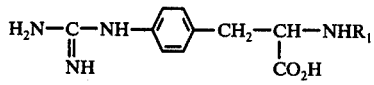

wherein $R_1$ is either hydrogen or a tert-butyl-oxycarbonyl group.

Particularly, the invention relates to a new compound formed of a tert-butyloxycarbonyl derivative of paraguanidino-L-phenylalanine, having the formula:

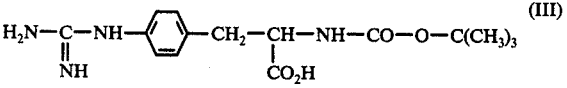

In accordance with a process of the invention, the compound of formula (III) is prepared starting from p-nitro-phenylalanine which, after its amine group has been protected, by a tert-butyloxycarbonyl group, is reduced so as to convert the $NO_2$ group into an amino-$NH_2$ group and the resulting derivative is reacted with a guanidination agent, such as 1-guanidino-3,5-dimethylpyrazole nitrate.

The above mentioned reduction is advantageously carried out with hydrogen in presence of a catalyst.

The guanidination step, to be really effective, must be carried out in an anhydrous organic solvent, in the presence of an organic base acting as a catalyst, at a temperature above 50° C., preferably at the reflux temperature of the solvent.

The compound (III) obtained is a valuable intermediate product for preparing other useful products, particularly the compound of formula (I), via compound (II).

Particularly, the compound IV obtained after removal of the tert-butyloxycarbonyl group of compound III, such as by acid hydrolysis, is transformed by action of a tosyl halide, e.g. tosyl chloride, into compound II.

Compound IV, having the formula

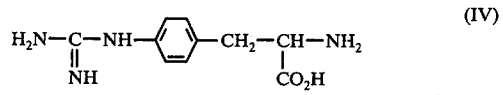

is obtained from compound III, such as by acid hydrolysis. It can also be reacted with the tosyl-halide to ultimately form the compound II.

The following methods of preparation are given by way of example and are non-limitative.

(1) Preparation of terbutyloxy-carbonyl-paraguanidino-phenyl-alanine.

3.10 g (10 m mols) of tert-butyloxy-carbonyl-paranitrophenyl-alanine are dissolved in 80 ml of methanol containing 0.6 ml acetic acid. The solution is kept at a temperature between 0° and 5° C. and hydrogenated for 3 hours in the presence of 500 mg of a catalyst comprising carbon containing 10% palladium. When the nitro groups have been reduced to amino groups, the catalyst is separated by filtration and the solvent is eliminated by distillation in vacuo. The residue is dried in the presence of $P_2O_5$ and NaOH. The reaction is quantitative. The product is dissolved in 20 ml tetrahydrofuran. 3.1 ml (19 m mols) diisopropylethylamine and 3 g (15 m mols) of 1-guanidino-3,5-dimethylpyrazole nitrate are successively added. The mixture is refluxed for 12 hours. The solvent is eliminated by distillation in vacuo. 40 ml methanol and 2.5 ml acetic acid are added to the residue. The product is placed in a refrigerator for a few hours, yielding a crystallized product which is separated by filtration and repeatedly washed with methanol at low temperature and dried with dry air. 2.6 gr (and 81% yield) is obtained of terbutyloxycarbonyl-p paraguanidino-L-phenylalanine.

The product has the following properties:
Elementary analysis:

| | C | H | N |
|---|---|---|---|
| Found % | 54.58 | 7.20 | 16.60 |
| Calculated % (for $C_{15}H_{22}O_4N_4 \cdot \frac{1}{2} H_2O$) | 54.45 | 6.99 | 16.91 |
| M.P. 198–200° C | | | |
| $[\alpha]_D^{25} + 28°$ (C = 1; $H_2O$ ) | | | |
| (Thin layer chromatography RF.0.55). | | | |

The product has a positive response to the Sakaguchi test (violet colour), a positive response to ultraviolet and a negative response to ninhydrin (becoming positive when the spot is heated).

(2) Preparation of paraguanidino-L-phenylalanine.

200 mg of terbutyloxycarbonyl-paraguanidino-L-phenylalanine are introduced into 2 ml of a mixture of trifluoroacetic acid, acetic acid and anisole in the proportions 7/3/1.

After 25 minutes, the acids are eliminated in vacuo and 50 ml dry ether is added. The precipitate is filtered, washed in dry ether and dried in vacuo in the presence of P$_2$O$_5$ and NaOH. All the product (200 mg) is dissolved in 5 ml acetic acid. 415 mg picric acid is added and the product is separated after a short time. The product is filtered, washed in acetic acid and dry ether, and dried in vacuo in the presence of P$_2$O$_5$ and NaOH.

120 mg (a 41% yield of paraguanidino-L-phenylalanine (monopicrate hemiacetate hemihydrate) is obtained, having
the following properties:
Elementary analysis:

|   | C | H | N |
|---|---|---|---|
| Found % | 41.65 |  | 19.80 |
| Calculated % | 41.65 | 4.19 | 19.74 |

(for the monopicrate hemiacetate hemihydrate)
C$_{10}$H$_{14}$O$_2$N$_4$ . C$_6$H$_3$O$_7$N$_3$ . ½ CH$_3$COOH . ½ H$_2$O)
M.P. 141–143° C (softens at 135° C)
$[\alpha]_D^{25}$ + 6° (C = 0.5; 50% acetic acid).

(3) Preparation of tosyl-para-guanidino-L-phenylalanine (or p-toluene-sulphonyl-p-guanidino-L-phenylalanine).

3 m mols (993 mg) tert-butyloxycarbonyl-para-guanidino-L-phenylalanine are dissolved in 6 ml of 5N hydrochloric acid. After 5 minutes, 15 ml acetic acid is added and the mixture is lyophilized. The residue is dissolved in 6 ml of 1 N sodium hydroxide. 10 ml tetrahydrofuran followed by 600 mg tosyl chloride in solution in 10 ml tetrahydrofuran are added in 5 portions over an hour. The pH of the mixture is kept between 8.5 and 9, using 1N sodium hydroxide. After 2 hours, the pH is adjusted to between 5 and 6 with acetic acid and the solvent is eliminated in vacuo. The product is kept for 12 hours at 0° C., filtered, washed with water and dried in the presence of P$_2$O$_5$.

The yield is 470 mg of a product melting at 275°–276° C. (thin-layer chromatography RF 0.51). The filtrate from the preceding operation is concentrated in vacuo, the water is poured off and methanol (1 ml) is added. Crystallization occurs. 5 ml water is added and, after a few hours, the operation is terminated in the previous manner, yielding 270 mg of product melting at 274°–275° C. The total yield, corresponding to 740 mg. of product is 63%.

For analysis, the product is dissolved in methanol and water is added. The product is again filtered then dried in a high vacuum at 100° C. for four hours.
The product obtained has the following properties:
Elementary analysis

|   | C | H | N | S |
|---|---|---|---|---|
| Found % | 53.65 | 5.45 | 14.30 | 8.30 |
| Calculated % | 53.5 | 5.65 | 14.28 | 8.17 |

(C$_{17}$H$_{20}$O$_4$S$_1$ . ½ CH$_3$OH)
M.P. 275 – 276° C
$[\alpha]_D^{25}$ + 24° (C = 1; 80% acetic acid)

(4) Preparation of paratoluene-sulphonyl-paraguanidino-L-phenylalanine methyl ester hydrochloride.

392 mg (1 m mol of the product prepared in 2) is suspended in 15 ml methanol. Hydrochloric acid is conveyed through the solution for 1 hour. The mixture is left for 12 hours, then concentrated in vacuo, adding 50 ml dry ether. The mixture is kept cold for a few hours, after which the ether is poured off and the residue is dried in vacuo in the presence of P$_2$O$_5$ and NaOH. The product is purified by chromatography on a column of the kind known commercially under the trade name Sephadex LH-20 (4 × 90 cm), the eluent being methanol. The flow rate is 20 ml per hour. The fractions are automatically separated according to the U.V. spectrum, each fraction being read at 280 mm. Fractions 135 to 146 contain the desired product, as was shown by thin-layer chromatography. The fractions are collected, the solvent is evaporated and the residue is dried in vacuo in the presence of P$_2$O$_5$, yielding 290 mg of an amorphous product (thin-layer chromatography RF 0.60).
Elementary analysis:

|   | C | H | N |
|---|---|---|---|
| Found % | 50.80 | 5.90 | 12.80 |
| Calculated % | 50.63 | 5.43 | 13.12 |

(C$_{18}$H$_{22}$O$_4$N$_4$S$_1$ . HCL)
$[\alpha]_D^{25}$ + 35° (C = 1; methanol).

Paratoluene-sulphonyl-paraguanidino-L-phenylalanine methyl ester has been found to be an excellent substrate for trypsin. Its activity as a substrate is about three times that of the compound used most usually for this purpose, i.e. TAME (toluene-sulphonyl arginine methyl ester).

This is shown by the following values for the constants k cat and Km, which are used to measure the "substrate activity".

|   | k cat | Km |
|---|---|---|
| Tosyl-para-guanidino-L-phenylalanine methyl ester | 413 sec$^{-1}$ | 5.45 × 10$^{-5}$ M |
| TAME (according to T. E. Barman, "Enzyme Handbook" Springer Verlag, Vol. II (1969)) | 147 sec$^{-1}$ | 5 × 10$^{-5}$ M |

Consequently, the substance is a very suitable reagent for the assay of trypsin activity.

We claim:
1. The tosyl-paraguanidino-L-phenylalanine methyl ester having the formula:

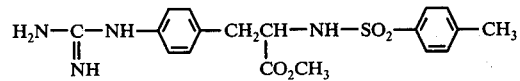

2. The salts of the compound of claim 1.
3. The hydrochloride of the compound of claim 1.

* * * * *

UNITED STATES PATENT AND TRADEMARK OFFICE
CERTIFICATE OF CORRECTION

PATENT NO. : 4,118,575
DATED : October 3, 1978
INVENTOR(S) : MEIR RIGBI et al

It is certified that error appears in the above–identified patent and that said Letters Patent are hereby corrected as shown below:

The "Assignee" in item [73] of the title page should read as follows:

"Choay, S.A., Paris, France and Yissum Research and Development Company of the Hebrew University of Jerusalem, Jerusalem, Israel, part interest each.

Signed and Sealed this

Sixteenth Day of January 1979

[SEAL]

Attest:

RUTH C. MASON
Attesting Officer

DONALD W. BANNER
Commissioner of Patents and Trademarks